United States Patent [19]

Sperry et al.

[11] Patent Number: 5,059,187

[45] Date of Patent: Oct. 22, 1991

[54] METHOD FOR THE CLEANSING OF WOUNDS USING AN AEROSOL CONTAINER HAVING LIQUID WOUND CLEANSING SOLUTION

[75] Inventors: Charles R. Sperry, Springfield, Vt.; Allan M. Raff, Walnut Creek, Calif.

[73] Assignee: Dey Laboratories, Inc., Napa, Calif.

[21] Appl. No.: 518,244

[22] Filed: May 4, 1990

Related U.S. Application Data

[63] Continuation of Ser. No. 277,895, Nov. 30, 1988, abandoned.

[51] Int. Cl.$^5$ ............................................. A61M 35/00
[52] U.S. Cl. ...................................... 604/290; 604/310; 128/66; 128/200.23
[58] Field of Search .................. 604/49, 54, 289, 290, 604/310; 128/200.14, 200.18, 200.21, 200.23, 65, 66; 222/206, 214, 217; 239/327, 328, 337

[56] References Cited

U.S. PATENT DOCUMENTS

| | | | |
|---|---|---|---|
| 1,378,481 | 5/1921 | Mobley | 128/200.23 |
| 1,614,532 | 1/1927 | Mobley | 128/200.23 |
| 1,892,750 | 1/1933 | Rotheim | 128/200.23 |
| 2,671,578 | 3/1954 | McBean | 222/214 |
| 2,686,081 | 8/1954 | Cooksley | 128/200.23 |
| 3,116,856 | 1/1964 | Prussin et al. | 239/337 |
| 3,186,645 | 6/1965 | Eberlein | 128/200.23 |
| 3,223,289 | 12/1965 | Bouet | 222/214 |
| 3,225,967 | 12/1965 | Heimgartner | 222/206 |
| 3,566,863 | 3/1971 | Law | 128/62 |
| 3,768,475 | 10/1973 | Osbourne | 222/394 |
| 3,791,557 | 2/1974 | Venus, Jr. | 222/214 |
| 3,836,079 | 9/1974 | Huston | 128/200.18 |
| 4,259,954 | 4/1981 | Scott | 604/310 |
| 4,350,158 | 9/1982 | Hudson | 604/310 |
| 4,784,652 | 11/1988 | Wilkström | 604/310 |
| 4,899,914 | 2/1990 | Schweigl et al. | 222/394 |

FOREIGN PATENT DOCUMENTS 8202034  6/1982  PCT Int'l Appl. ................. 222/214

OTHER PUBLICATIONS

Stevenson et al., Journal of American College of Emergency Physicians, 1/78, vol. 5, #1, pp. 17-21.

Primary Examiner—John D. Yasko
Assistant Examiner—Anthony Gutowski
Attorney, Agent, or Firm—Flehr, Hohbach, Test, Albritton & Herbert

[57] ABSTRACT

Method for irrigating a wound and/or abrasion with a liquid wound cleansing solution dispensed from a hand-held container with the liquid wound cleansing solution disposed therein and to be dispensed through a manually operable valve. The method includes the steps of providing a propellant in the container which provides a pressure for propelling the wound cleansing solution through the valve, actuating the manually actuated valve to provide a stream of liquid wound cleansing solution which is substantially equivalent in volume and in pressure to that generated by a human hand-held 30 to 60 milliliter syringe having an 18 gauge needle mounted thereon and directing the stream toward the wound or abrasion to irrigate and cleanse the wound and/or abrasion.

6 Claims, 2 Drawing Sheets

METHOD FOR THE CLEANSING OF WOUNDS USING AN AEROSOL CONTAINER HAVING LIQUID WOUND CLEANSING SOLUTION

CROSS REFERENCE TO RELATED APPLICATION

This is a division of application Ser. No. 277,893 filed Nov. 30, 1988 (now abandoned).

FIELD OF THE INVENTION

This invention relates to an aerosol container for cleaning of wounds and a method.

BACKGROUND OF THE INVENTION

In the cleaning of in hospitals and clinics it is generally the practice to utilize syringes which can be held and operated by the human hand and which are typically provided with 18 gauge needles. These syringes typically have a capacity ranging from 30 to 60 milliliters and typically must be filled several times with a wound cleansing solution in order to achieve the desired volume of the wound cleansing solution needed for cleaning the wound. With the advent of AIDS, it has become very desirable to minimize or eliminate the use of needles wherever possible. Attempts have been made to solve this problem by the use of collapsible squeeze bottles containing a wound cleansing solution. However, it has been found that wound cleansing solution dispensed from such hand-held squeeze bottles is not as efficacious as the streams delivered from the 18 gauge needles carried by syringes heretofore utilized. There is therefore a need for an improved solution for avoiding the uses of needles and syringes in the treatment of wounds and/or abrasions with normal cleansing solutions.

SUMMARY OF THE INVENTION

In general, it is an object of the present invention to provide an aerosol hand-held container and method for the cleaning of wounds.

Another object of the invention is to provide a container and method of the above character in which the container and method provides a stream of wound cleansing solution substantially equivalent to that produced by a hand-held syringe carrying an 18-gauge needle.

Another object of the invention is to provide an aerosol container and method of the above character which avoids the use of needles.

Another object of the invention is to provide an aerosol container and method of the above character in which the container contains enough wound cleansing solution to irrigate the average wound or abrasion.

Another object of the invention is to provide an aerosol container of the above character in which pressurized stream of wound cleansing solution can be produced in any position of the aerosol container. Another object of the invention is to provide an aerosol container of the above character in which the wound cleansing solution can be sterilized.

Another object of the invention is to provide an aerosol container of the above character in which irradiation is not required for sterilization.

Additional objects and features of the invention will appear from the following description in which the preferred embodiments are set forth in detail in conjunction with the accompanying drawings.

DESCRIPTION OF THE PREFERRED EMBODIMENTS

In general, the aerosol container of the present invention utilized for cleaning of wounds is comprised of a rigid container adapted to withstand pressures of at least 100 psi. A wound cleansing solution is carried within the container. A valve assembly is carried by the container and is in communication with the solution in the container and is movable between open and closed positions. A gas propellant is disposed in the container. The valve assembly has a nozzle which when the valve assembly is moved to an open position and in combination with the wound cleansing solution and the pressure created by the gas in the container creates a pressurized stream of wound cleansing solution which is substantially equivalent to that which is generated by a human hand operating a 30 to 60 milliliter syringe having an 18 gauge needle mounted thereon. In certain embodiments of the aerosol container, a collapsible pouch is provided within the container which contains the wound cleansing solution. The propellant gas is disposed outside of the collapsible pouch.

In the method for cleaning a wound or abrasion, a wound cleansing solution is provided which is formed into a pressurized stream which is substantially equivalent to that which is generated by a human hand operating a 30 to 60 milliliter syringe having an 18 gauge needle mounted thereon. The pressurized stream is created by the use of a prop gas.

Figures 1, 2:
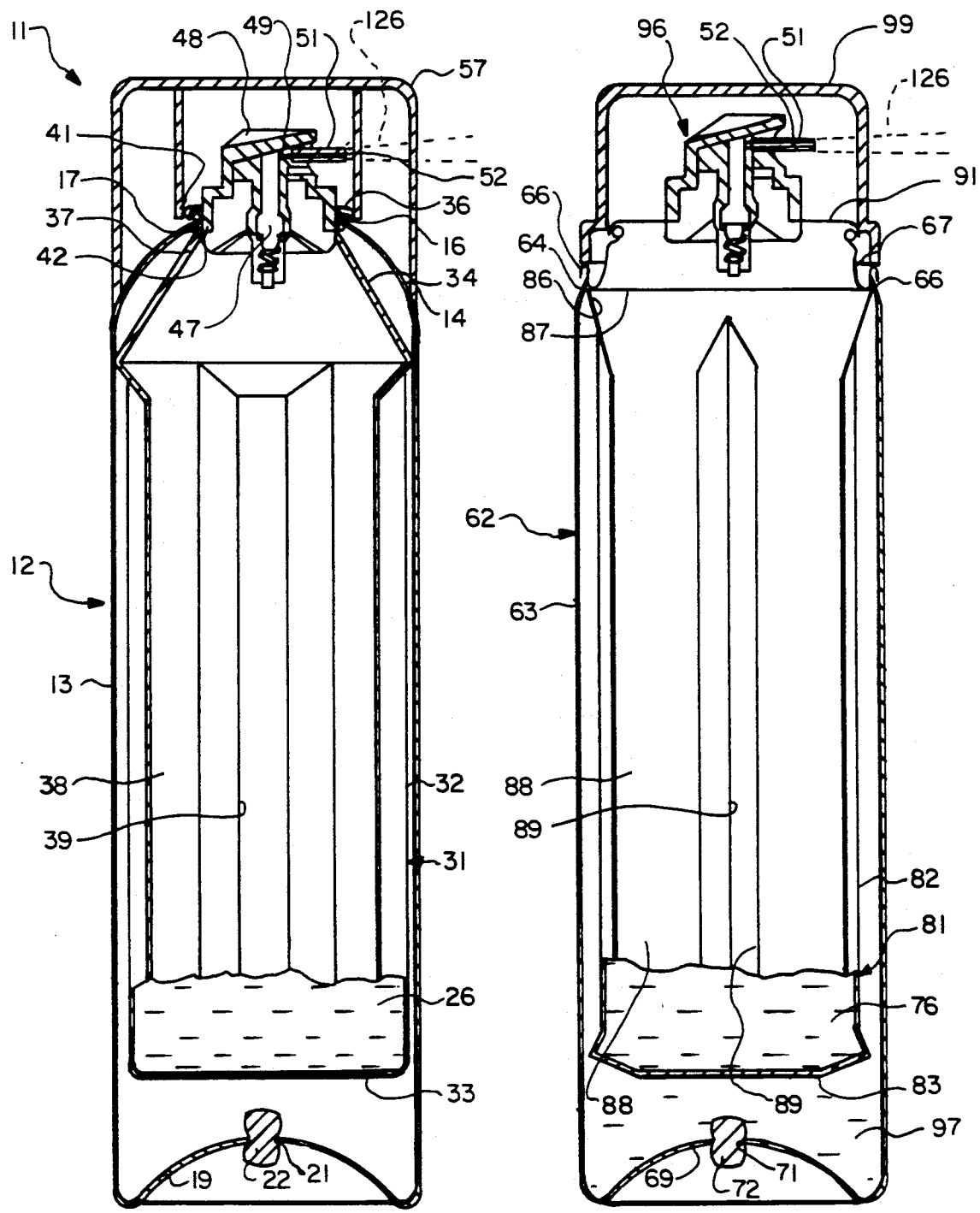
FIG. 1 is a side elevational view partially in cross section showing an aerosol container utilizing a collapsible plastic pouch incorporating the present invention.
FIG. 2 is an another embodiment of the aerosol container of the present invention utilizing a collapsible metallic pouch.

More in particular, the hand-held aerosol container 11 as shown in FIG. 1 consists of a cylindrical seamless drawn can 12 formed of a suitable material such as aluminum and of a size that can readily fit in an adult human hand. The can 12 is provided with a cylindrical side wall 13 that has its upper extremity provided with an inwardly rounded shoulder 14 with the upper extremity of the side wall 13 being formed with an inwardly curled bead 16 to provide a central opening 17. The can 12 is provided with a bottom wall 19 which is concave as shown in FIG. 1. It is provided with an opening 21 which has a removable plug 22 mounted therein formed of a suitable material such as rubber that is utilized for introducing a propellant into the can as hereinafter described.

A wound cleansing solution 26 of a conventional type is provided within the can 12. For example the wound cleansing solution can be a sodium chloride or saline solution 0.9% w/v U.S.P. in sterile purified water with benzalkonium chloride 0.004 w/v. If the aerosol container 11 is subjected to gamma ray radiation for sterilization, it is desirable to adjust the saline solution with 0.1N sodium hydroxide upward in pH to anticipate the pH drop caused by the gamma ray radiation.

The wound cleansing solution 26 in the embodiment of the invention shown in FIG. 1 is carried or contained within a flexible and collapsible pouch 31. The pouch 31 can be of any desired shape. However, in order to provide the maximum volume which can be utilized in the can 12 it is desired that it have a generally cylindrical configuration closely approximating that of the can 12. Thus it is provided with a cylindrical side wall 32 which is spaced relatively closely to the side wall 13 of the can 12. It is also provided with a bottom wall 33 which is spaced above the bottom wall 19 of the can to provide space for a propellant as hereinafter described. The upper portion of the pouch 31 is provided with an inwardly and upwardly tapered side wall 34 which terminates in a rounded lip 36 that is adapted to overlie the bead 16 to provide a central opening 37 which opens into the interior of the pouch 31. In order to facilitate collapsing of the pouch 31, the cylindrical side wall 32 can be provided with vertically extending spaced apart parallel ribs 38 and recesses 39. The pouch 31 can be formed in a suitable manner such as by molding the same from a high density polyethylene. The can 12 and the pouch 31 can be of a type manufactured and sold by Lechner GMBH.

The wound cleansing solution 26 which is to be utilized in the container can be introduced through the opening 37 to substantially fill the pouch 31. After the filling has been completed, a cap 41 of a conventional type formed of a suitable material such as aluminum is crimped over the bead 16 and over the lip 36 to close the opening 37 and to provide a liquid and air-tight seal between the upper extremity of the can 12 and the cap 41. The cap 41 is provided with a cup-shaped recess 42. A valve assembly 46 is provided as a part of the cap 41 and is centrally mounted in the recess 42. The valve assembly 46 is provided with a valve 47 and an actuator 48. The valve assembly 46 can be of a conventional type such as supplied by Precision Valve Corporation of Yonkers, N.Y. 10702. The actuator 48 is provided with an orifice of a predetermined size, as for example, ranging from 0.015 to 0.030 inches and preferably a diameter of approximately 0.019 inches. In accordance with the present invention, an extension tube 51 is mounted in the actuator 48 and is provided with a flow passage 52 therein having a diameter corresponding to the diameter of the orifice 49.

A cap 57 is removably mounted by a friction fit on the top of the can 12 and encloses the valve assembly 46.

A suitable propellant 56 is introduced into the interior of the can 12 through the opening 21 in a conventional manner and the plug 22 is thereafter inserted. Compressed air or nitrogen can be utilized as the propellant. It has been found that it is desirable to utilize a ratio of approximately 60:40 for the product to propellant by weight utilizing either the compressed air or nitrogen. In order to achieve an improved product to propellant ratio other propellants can be utilized. For example, Dymel 22A, a product of DuPont can be utilized. The Dymel 22A has a 60:40 ratio of chlorodifluoromethane and dimethylether. Dymel 22A yields a pressure of 68 psi gauge (psig). Utilizing this method a 97:3 product to propellant ratio can be achieved.

Another embodiment of the invention is shown in aerosol container 61 in FIG. 2. It consists of a can 62 which is cylindrical and seamless and which is provided with a side wall 63 having an inwardly rounded shoulder 64 and terminating in a rim 66 to define an opening 67. It is also provided with a bottom wall 69 which is concave in shape and which has a hole 71 provided therein which receives a rubber plug 72. A wound cleansing solution 76 of the type hereinbefore described is provided within the can 62 and is disposed within a pouch 81. The pouch 81 differs from the pouch 31 in FIG. 1 in that it is formed of a thin metal, as for example, aluminum rather than high density polyethylene. It has been found that the use of the metal pouch is desirable because it can be autoclaved. This pouch 81 is provided with a cylindrical side wall 82 and a bottom wall 83 spaced above the bottom wall 69. The pouch 81 is provided with an inwardly extending rim 86 which defines an opening 87. The pouch is provided with vertically extending spaced apart parallel ribs 88 and recesses 89. The container 61 and the pouch 81 also can be of a type which is available from Lechner GMBH. A cap 91 is provided and is crimped over the rim 86 of the pouch 81 and of the rim 66 of the can 62 to form a hermetic seal between the same which is fluid-tight and so that the pouch 81 is suspended in the can 62 to provide a flanged rim 92 for the container as shown in FIG. 2. A valve assembly 96 is mounted in the cap 91 and is of the same type as the valve assembly 46 hereinbefore described. A propellant 97 is introduced into the can 22 through the hole 71. In utilizing compressed gasses as a propellant where ratios of 60:40 for product to propellant can be obtained. In utilizing a liquid gas propellant, a ratio of 70:30 to 97 to 3 can be obtained. A removable cap 99 similar to cap 57 is provided in the can 62. In one version of this embodiment of the invention 220 grams of the wound cleansing solution were introduced into the Pouch 81 and 6 grams of Dymel 22A were introduced into the container 101. With an orifice of 0.018 the wound cleansing solution was dispensed at a rate of 3.2 milliliters per second over a period of 70 seconds.

Figure 3:
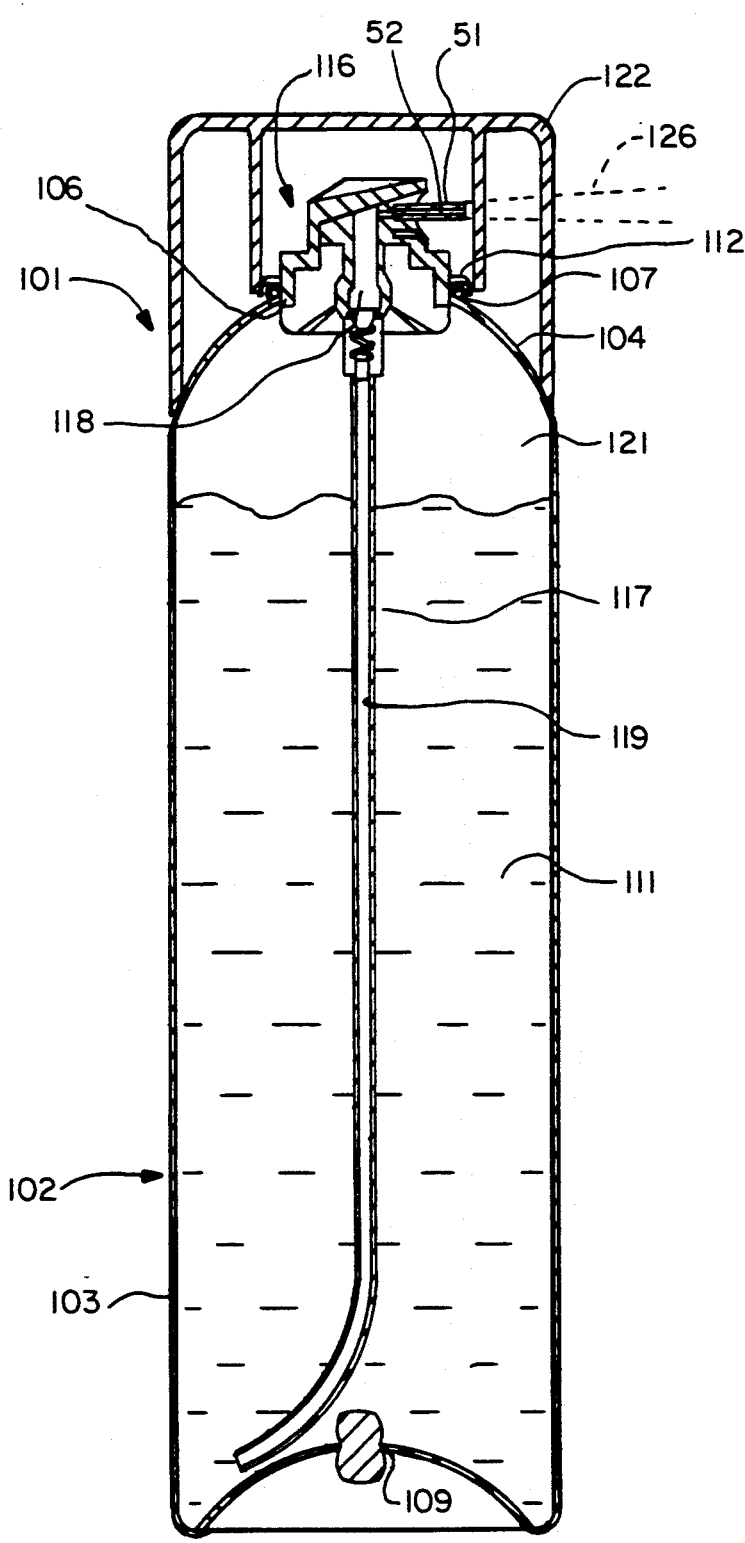
FIG. 3 is a cross sectional view of still another embodiment of an aerosol container incorporating the present invention.

Still another embodiment of an aerosol container incorporating the present invention is shown in the container 101 shown in FIG. 3. The container 101 consists of a can 102 formed of a suitable material such as extruded aluminum. It is cylindrical and seamless and is provided with a cylindrical side wall 103 which is provided with an inwardly curved shoulder 104 that terminates in a rim 106 to provide an opening 107. The can is also provided with a bottom wall 109 which is concave.

A wound cleansing solution 111 is disposed within the can 102. A cap 112 is provided for closing the opening 107 and is crimped onto the rim 106 to provide a fluid-tight seal between the rim 106 and the cap 112. The cap 112 is provided with a valve assembly 116 similar to the valve assemblies 46 and 96 hereinbefore described. Since a pouch is not utilized in this embodiment of the invention, it is necessary to provide a standpipe or dip tube 117 which is connected to the valve 118 of the valve assembly 116. The dip tube 117 can be formed of a suitable material such as polyethylene. A cap 122 is removably mounted on the can 102. The dip tube 117 has a length so that it extends downwardly from the valve 118 to a position adjacent the bottom wall 109 as shown in FIG. 3 and is provided with a flow passage 119 which is in communication with the valve 118. A propellant 121 is provided in the space in the can 103 which is not occupied by the wound cleansing solution 111 and can be introduced through the valve assembly 116. A cap 122 is removably mounted on the can 102.

In the production of the products shown in FIGS. 1, 2 and 3, various procedures can be utilized. For producing the product shown in FIG. 3, the wound cleansing solution 111 can be introduced into the can 103 through the opening 107. The cap 112 can then be crimped onto the can 102. The propellant gas such as nitrogen can then be introduced through the valve assembly 116. Thereafter, the container 101 with the wound cleansing solution therein can be sterilized by the use of gamma irradiation.

In the production of the products shown in FIGS. 1 and 2, the wound cleansing solution is introduced into the pouch outside the can or after the pouch is in the can and thereafter placing the cap on the can and crimping it into place. Before introducing the propellant, the container with the pouch therein can be autoclaved at a suitable temperature, as for example, 120° to 130° C. for a suitable period of time ranging from 20 to 45 minutes, and preferably a period of approximately 30 minutes. After autoclaving has been accomplished and the container has cooled, a propellant can be introduced through a hole in the bottom wall and then closing the hole with the rubber stopper or plug hereinbefore described.

It should be appreciated that in accordance with the present invention, containers of various sizes can be provided. However, for the present application in which a wound cleansing solution is utilized for cleaning wounds, abrasions and the like, it has been found desirable to provide a container which is capable of receiving a liquid fill in the order of 225 cubic centimeters. It also should be appreciated that various pressures can be utilized within the container for expelling the wound cleansing solution from the container. However, it has been found that initial pressures ranging from 60 to 100 psig for a propellant gas can be used with an orifice of 0.015 to 0.030 inches in diameter actuation of the valve assembly to provide a stream 126 of the wound cleansing solution discharged at a flow rate varying from approximately 8 cubic centimeters per second down to approximately 3 cubic centimeters per second at a point in time when the container is nearly empty of the wound cleansing solution. The average flow is approximately 5 cubic centimeters per second. The entire container can be emptied in approximately ½ to 1 minute. It has been found that it is preferable to have the minimum design discharge rate be approximately 4 cubic centimeters per second or greater. Utilizing a propellant such as Dymel 22A it is possible to achieve a substantially constant flow rate throughout the discharge of the contents of the container.

Utilizing such parameters, it has been found that for the embodiment of the present invention, shown in FIG. 3, the volume of wound cleansing solution delivered through the extension tube 51 is at least approximately 60% of the total wound cleansing solution in the container with a product to gas ratio of 70% to 30% and initial pressure of approximately 90 psig.

The aerosol containers of the present invention for irrigating wounds and/or abrasions of the skin are far more efficacious than syringes utilized in the past. By way of example, it has been found that a 3×6 inch target area having the wound therein can be cleaned utilizing the aerosol container of the present invention in approximately 30 seconds whereas the same type of cleaning utilizing a syringe required approximately 135 seconds. The additional time required for use of the syringe was principally due to the fact that the syringe had a limited volume and had to be refilled, as for example, as many as 6 times to accomplish the same amount of cleaning action.

It was found that with the above parameters it is possible to provide a stream 126 of wound cleansing solution which has approximately the same characteristics as that produced by a hand-held 30 to 60 milliliter syringe provided with an 18 gauge needle.

In the embodiment of the aerosol container shown in FIG. 3, a dip tube is utilized which requires that the container be maintained in a generally upright position in order to have the wound cleansing solution enter the bottom of the dip tube. When the container is inverted, the gas propellant surrounds the open extremity of the drip tube and precludes the wound cleansing solution from being ejected by the container. However, with the embodiments of the aerosol container shown in FIGS. 1 and 2, this difficulty is overcome because these aerosol containers can be held in any position and still cause a stream of wound cleansing solution to be expelled therefrom. In addition, the aerosol container shown in FIGS. 1 and 2 have other advantages. For example, as hereinbefore described autoclaving can be utilized for the containers having metal pouches eliminating the necessity for radiation to obtain sterilization. In addition, since the wound cleansing solution is separated from the propellant by the use of the pouches which serve as barriers, a gas such as butane or a liquid and gas such as Dymel 22A can be utilized making it possible to obtain a substantially constant pressure throughout the expelling of the product or wound cleansing solution contained in the aerosol container.

In general, the hand-held aerosol container of the present invention has numerous advantages for irrigating wounds and abrasions. It is easy to use. It is convenient. It can be used quickly. It is relatively compact. It provides a stream of wound cleansing solution which has the same characteristics as that provided by the 18 gauge needle carried by a syringe conventionally utilized by doctors in the past. A more constant uniform flow rate is provided for the wound cleansing solution stream. The aerosol containers can be readily stored so that they are available for immediate use.

What is claimed is:

1. In a method for irrigating a wound and/or abrasion with a wound cleansing aqueous saline solution of approximately 0.9% w/v dispensed from a hand-held aerosol container with the liquid wound cleansing solution disposed therein and to be dispensed through a manually operable valve, providing a propellant in the container which provides a pressure for propelling the wound cleansing solution through the valve, sizing the valve and selecting the pressure whereby when the manually actuated valve is activated, it provides a stream of liquid wound cleansing solution which is substantially equivalent in volume and in pressure to that generated by a human hand-held 30 to 60 milliliter syringe having an 18 gauge needle mounted thereon and grasping the container with the hand, actuating the valve with the same hand and positioning the hand with the container therein to direct the stream of wound cleansing solution coming from the valve toward the wound or abrasion to irrigate and cleanse the wound and/or abrasion.

2. A method as in claim 1 together with the step of providing a pressure on the wound cleansing solution ranging from 60–100 psig.

3. A method as in claim 1 wherein the liquid wound cleansing solution is disposed in a collapsible pouch, wherein the collapsible pouch is disposed in a container and wherein the propellant is disposed in the container outside the collapsible pouch.

4. In a method for irrigating a wound and/or abrasion with a wound cleansing aqueous saline solution of approximately 0.9% w/v dispensed from a hand-held self-contained container having a finger-actuated valve thereon, placing the liquid wound cleansing solution in the container and providing a propellant in the container, sizing the valve and selecting the pressure so that when the valve is operated it provides a stream of wound cleansing solution which is substantially equivalent in volume and pressure to that generated by a hand-held 30 to 60 milliliter syringe having an 18 gauge needle mounted thereon, picking up and grasping the container in one hand, operating the valve with a finger of said one hand and positioning said one hand to direct the stream of wound cleansing solution into the wound and/or abrasion to irrigate and cleanse the wound and/or abrasion.

5. A method as in claim 4 together with the step of placing the wound cleansing solution in a collapsible pouch in the container with the propellant surrounding the pouch whereby the stream can be provided in any position of the container.

6. A method as in claim 4 in which the wound cleansing solution is dispensed at a minimum rate of about four cubic centimeters per second.

* * * * *